(12) United States Patent
Tol

(10) Patent No.: US 10,441,789 B2
(45) Date of Patent: Oct. 15, 2019

(54) INTERFACE MEANS, ESPECIALLY AN INTERFACE MEANS FOR A MEDICAL DEVICE

(71) Applicant: MEDTRONIC BAKKEN RESEARCH CENTER B.V., Maastricht (NL)

(72) Inventor: Jeroen Jacob Arnold Tol, Eindhoven (NL)

(73) Assignee: Medtronic Bakken Research Center, B.V., Maastricht (NL)

( * ) Notice: Subject to any disclaimer, the term of this patent is extended or adjusted under 35 U.S.C. 154(b) by 61 days.

(21) Appl. No.: 14/440,289

(22) PCT Filed: Oct. 30, 2013

(86) PCT No.: PCT/EP2013/072718
§ 371 (c)(1),
(2) Date: May 1, 2015

(87) PCT Pub. No.: WO2014/068002
PCT Pub. Date: May 8, 2014

(65) Prior Publication Data
US 2015/0297892 A1     Oct. 22, 2015

Related U.S. Application Data

(60) Provisional application No. 61/721,955, filed on Nov. 2, 2012.

(30) Foreign Application Priority Data

Nov. 2, 2012 (EP) .................................... 12191135

(51) Int. Cl.
*A61N 1/36* (2006.01)
*A61N 1/05* (2006.01)
(Continued)

(52) U.S. Cl.
CPC ........ *A61N 1/36125* (2013.01); *A61B 5/0478* (2013.01); *A61N 1/0534* (2013.01); *A61N 1/36185* (2013.01); *A61N 1/37217* (2013.01)

(58) Field of Classification Search
CPC ............ A61N 1/36125; A61N 1/37217; A61N 1/0534; A61N 1/36185; A61B 5/0478
See application file for complete search history.

(56) References Cited

U.S. PATENT DOCUMENTS

| 5,003,975 | A | 4/1991 | Hafelfinger et al. |
| 5,571,156 | A | 11/1996 | Schmukler |

(Continued)

FOREIGN PATENT DOCUMENTS

| WO | 2011107917 A1 | 9/2011 |
| WO | 2014068002 A1 | 5/2014 |

OTHER PUBLICATIONS

International Preliminary Report on Patentability from International Application No. PCT/EP2013/072718, dated May 14, 2015, 7 pp.

(Continued)

*Primary Examiner* — Rex R Holmes
(74) *Attorney, Agent, or Firm* — Shumaker & Sieffert, P.A.

(57) ABSTRACT

The present invention relates to an interface means, especially an interface means for a medical device, comprising at least one or more lines, whereby the lines are configured such that each line has at least one specific functionality and/or is able to connect a first connection means with a second connection means, and at least one grouping and/or redistributing means, wherein the at least one grouping and/or redistributing means is configured such that the lines can be grouped and/or redistributed onto one or more lines and/or the functionality of lines can be grouped and/or redistributed onto one or more lines, preferably onto at least one single line. Furthermore, the present invention relates to (Continued)

Figure 1:
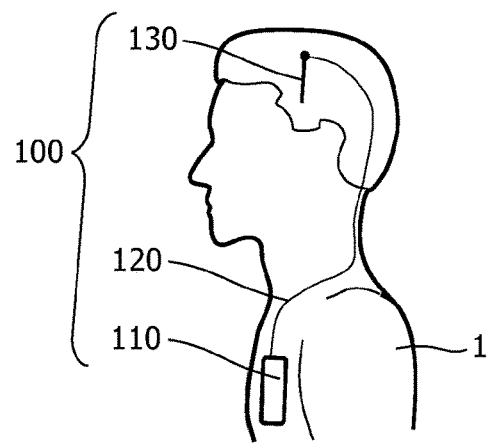

a method for communicating a plurality of signals, in particular power and/or data signals and/or control signals, over a plurality of lines.

18 Claims, 8 Drawing Sheets

(51) Int. Cl.
*A61B 5/0478* (2006.01)
*A61N 1/372* (2006.01)

(56) References Cited

U.S. PATENT DOCUMENTS

| | | | | |
|---|---|---|---|---|
| 5,814,088 | A | * | 9/1998 | Paul ............... A61N 1/3706 607/28 |
| 5,941,906 | A | * | 8/1999 | Barreras, Sr. ...... A61N 1/36071 607/60 |
| 6,473,653 | B1 | | 10/2002 | Schallhorn et al. |
| 8,027,737 | B2 | * | 9/2011 | Kokones ............. A61N 1/0529 607/115 |
| 2003/0149456 | A1 | * | 8/2003 | Rottenberg .......... A61N 1/3752 607/37 |
| 2007/0225674 | A1 | | 9/2007 | Molnar et al. |
| 2008/0046023 | A1 | | 2/2008 | Fischell |
| 2009/0118787 | A1 | | 5/2009 | Moffitt et al. |
| 2010/0023084 | A1 | | 1/2010 | Gunderson |
| 2010/0100153 | A1 | | 4/2010 | Carlson et al. |
| 2012/0191153 | A1 | | 7/2012 | Swerdlow et al. |

OTHER PUBLICATIONS

Extended European Search Report from European Application No. 12191135.8, dated Mar. 6, 2013, 7 pp.
Response to Examination Report dated Jan. 25, 2017 from counterpart European Application No. 13788926.7 filed Jun. 1, 2017, 6 pp.
Examination Report from counterpart European Application No. 13788926.7, dated Jan. 25, 2017, 4 pp.
International Search Report and Written Opinion from International Application No. PCT/EP2013/072718, dated Jan. 8, 2014, 10 pp.

* cited by examiner

INTERFACE MEANS, ESPECIALLY AN INTERFACE MEANS FOR A MEDICAL DEVICE

The present invention relates to an interface means, especially to an interface means for a medical device and a system for neural applications, in particular for brain applications. The invention also relates to a method for communicating a plurality of signals over a plurality of lines.

Implantable neurostimulation devices have been used for the past 10 years to treat acute or chronic neurological conditions. Deep brain stimulation (DBS), the mild electrical stimulation of sub-cortical structures, belongs to this category of implantable devices, and has been shown to be therapeutically effective for Parkinson's disease, Dystonia, and Tremor. New applications of DBS in the domain of psychiatric disorders (obsessive compulsive disorder, depression) are being researched and show promising results. In existing systems, the 1.27 mm-diameter, 10-50 cm-long probes carry 4 annular electrodes at the distal end, that are connected to the Implantable Pulse Generator (IPG) using a 3.8 mm-diameter, 4 screw-contacts connector, by means of 2.8 mm-diameter extension cables. The proximal end of the probe has four concentric contacts that fit into the 4-contacts connector of the extension cable, thereby electrically connecting each electrode to the outputs of the IPG through a so-called "header".

Future systems will need more, smaller electrodes, in order to better control the delivery of electrical stimulation, because current stimulation causes mild to severe side-effects in about 30% of the patients. A larger number of electrodes means a larger number of contacts to the connector, which in turn calls for different connector technologies, because it cannot be expected from the neurosurgeon to tighten more than 10 individual screws for the more than 10 contacts. Also, the contact sizes need to be smaller, certainly in the case of cranial implants.

One drawback of existing neurostimulation is that existing neurostimulation devices can only address a small number of electrodes, in particular 16 electrodes as a maximum, due to practical limitations on the number of connections that can be connected intra-operatively. Furthermore, due to the fact that existing implantable pulse generators should be modified as little as possible for cost reasons and for back-compatibility considerations, any improvements should leave the design of the implantable pulse generator modified as little as possible.

Among other applications, the interface means and the method of the present invention can be used as a part of a system for deep brain stimulation. In deep brain stimulation, electrical signals are sent to specific areas of the brain. The signals are applied using an implant, typically a lead, which comprises a plurality of stimulation electrodes at its distal end. In modular implants, wired interfaces are often used not only to establish a communication channel between the different modules of the implant but also to transport power and therapeutic signals between modules. The reliability of such a wired interface is crucial from both safety and therapeutic point of view.

Wire redundancy can be used to increase the reliability of an interface in a situation where a wire is, for example, broken or shorted. However, the application of redundancy in itself has several disadvantages: Firstly, an increase in cable dimensions is created, which is often not allowed for mechanical and medical reasons. Secondly, a reduced wire diameter to stick with maximum allowable cable dimensions is created, which makes the individual wires more vulnerable, reducing their reliability and/or their compliance with electronic and mechanical requirements. Thirdly, costs are increased both due to the more expensive cable as well as the higher number of connections that need to be made.

In view of the above, it is an object of the present invention to provide an interface means and a system for neural applications and a method that overcome some or all of the above problems, in particular in that a wired interface concept may be provided, which maximizes the interface cable reliability with a minimum wire redundancy.

The above object is solved according to the present invention with an interface means with the features of claim 1. Accordingly, an interface means, especially an interface means for a medical device, is provided whereby the interface means comprises at least one or more lines, whereby the lines are configured such that each line has at least one specific functionality and/or is able to connect a first connection means with a second connection means, and at least one grouping and/or redistributing means, wherein the at least one grouping and/or redistributing means is configured such that the lines can be grouped and/or redistributed onto one or more lines and/or the functionality of lines can be grouped and/or redistributed onto one or more lines, preferably onto at least one single line.

The lines can be for example wires, in particular wires that are individually insulated and bundled together as part of a cable.

Grouping and/or redistributing of lines onto one or more lines can refer to redistributing the functionality of several lines onto one or more lines. For example, if only a smaller number of physical lines is available, n (functional) lines are redistributed onto m<n (physical) lines.

Furthermore, redistribution can be performed if, for example, in neural recording more bandwidth is required. In this case (and also in other cases), the grouping/redistributing results in the functionality of one line being spread over several lines, e.g. in order to achieve a higher bandwidth. Further, it is possible that e.g. the functionality of one line is spread across one or more additional line(s) in order to create redundancy.

According to the invention, the advantage is achieved that a wired interface concept may be provided, which maximizes the interface cable reliability with a minimum wire redundancy. By means of the invention, an increase of the cable dimensions is prevented and it is possible to comply with the given mechanical and medical circumstances. Further, the costs are in control and reduced when compared with systems having similar functionality, reliability and redundancy, since the costs for the cable are lower and fewer connections must be provided.

The connection means can be connection points to signal sources or sinks. For example, a line can be connected to a first connection means, which is the source of a signal and the second connection means is the corresponding receiving point of this signal. The connection means can also provide connections to a ground line and a supply voltage.

The grouping and/or redistributing means can be implemented using (e.g. electronically controlled) switches that can be configured to connect the lines with different connection means. In particular, the grouping and/or redistributing means can be configured to connect a line with none of the provided first connection means, exactly one of the first connection means or with several first connection means. The same applies for the second connection means.

The proposed robust interface concept is based on the idea that the interface's functionality can be (re)distributed across a smaller number of lines if (partial) failure of one or more lines of the interface is detected. This adjustment (which can be performed automatically) strives to maintain the interface's full functionality or let it degrade gracefully, for example, by keeping the most vital functions of the interface running and/or enable a safe mode on the modular implant.

In other embodiments, the functionality can also be redistributed across a larger number of lines, as it can still be desirable to have wire redundancy in combination with a reconfigurable interface.

The reconfigurability can lead to a much higher overall reliability than just extending the interface cable with more lines.

According to the invention, electronics which makes use of the inherent line redundancy can be added to an interface cable if a multi line interface cable is applied. If one or more lines of the cable fails or becomes electronically unusable, which has to be detected by the implant anyway, the added electronics can (re)distribute the interface's functionality over the remaining lines. In the limit, if the interface requirements allow, the last remaining functional line of the interface cable can be used for all or the most vital interface functions, in which case the implant remains (partially) operational till the "last line standing".

If this approach to (re)distribute interface functionality in case of line failure is chosen, one should realize that this is only useful if it pays off to use all the available lines in normal operation where a 100% intact interface cable is assumed. Otherwise, it is better to distribute the interface functions over fewer lines. Thus only if all the trade offs in the interface design space (power, complexity, mechanics, costs etc.) lead to an interface cable with more than a single line, the ground line (most likely) excluded, the mentioned approach leads to significant increase in interface reliability.

The other way around, if a single line interface turns out to be the best solution, one can add extra lines to the interface cable, assuming this option lies in the allowable design space and (thus) also leads to higher reliability, and add electronics to choose another line if the applied line fails.

In both cases of a multiple and single line interface (with line redundancy), adding electronics to (re)distribute interface functionality also opens up the way to apply this if, for example, more power or data communication is required. Thus one can optimize interface reliability for a specific operation condition (for example in "stimulation" mode) with the presented approach, while the availability of multiple cable lines can advantageously be used in non critical conditions (for example in "recording" mode to increase the effective bandwidth of the lined interface) where reliability is of no or lesser concern.

According to another aspect of the present invention, the at least one grouping and/or redistributing means is configured such that the line(s) and/or the functionality of the line(s) is grouped and/or redistributed onto one or more lines, if it is detected that one or more lines become(s) unusable for its/their purpose.

Detecting whether lines are unusable allows to automatically react to a failing line and to redistribute the functionality of the lines across the smaller number of lines that are still available. If it is detected that two (physical) lines are shorted, the grouping and/or redistributing means can treat the shorted lines as only one line. For example, the same signals can be sent over both lines, such that the interface means operates consistently even if the detected short between the two lines is later on eliminated. For example, when a short is detected between two lines, those two lines can be shorted in the ICPSM and subsequently treated as a single (functional) line. The same signals can be sent across the two (physical) shorted lines via reconfiguration of the electronics on both sides of the interface. (The lines are shorted twice: the inherent detected short and the short that is deliberately created in the ICPSM).

According to another aspect of the present invention, at least one line is a pulse generator line being connectable to a pulse generator output (PG1) and/or a data input line and/or an output line (DATA IN/OUT) and/or a power line and/or a clock line (PWR/CLK) and/or a connection line for ground (GND).

According to this aspect of the invention, the lines are assigned certain functionalities. If one of the lines fails and becomes unusable for its purpose, the functionality can be distributed to the other lines.

According to yet another aspect of the invention, at least one of the lines is a connection line for ground and the grouping and/or redistributing means is configured such that the connection line for ground (GND) can be replaced by at least one conductive means being in conductive contact with the interface means.

In particular, it is possible that the conductive means is a means of low(er) conductivity. For example, the conductive means can be the tissue of a patient surrounding the lines or other parts of the interface means if the interface means is an interface means for a medical device which is attached to or embedded into the patient. Advantageously, the conductivity can be improved by equipping the interface means with a large conductive surface, which is in contact with the skin or tissue of the patient. Moreover, it is possible that e.g. in cases when the connection line for battery ground is redistributed, the connection line for battery ground can be replaced by at least some parts of a housing of the active lead can and/or by at least one conductive means being in conductive contact with the active lead can.

The interface means can be in contact with the conductive means at two different locations and between these two locations the conductive means can take over the role of a line that has failed.

According to another aspect of the invention, the at least one grouping and/or redistributing means comprises at least one cross-point switch matrix means.

A crosspoint switch matrix means with the dimensions m*n can comprise m*n switches and can be configured such that it can connect each of the m column connectors with each of the n row connectors. For example, the lines of the present invention can be connected with the row connectors of the crosspoint switch matrix means and the connection means can be connected with the columns of the crosspoint switch matrix means. In a preferred embodiment, the cross point switch matrix means comprises electronic switches and is controllable through an electronic controller.

According to another aspect of the invention, the interface means further comprises a cable monitor that is configured to monitor a usability of the lines, in particular a resistance of the lines and/or short-circuits between different lines.

Monitoring the lines for their usability has the advantage that a line failure can be automatically detected and the functionality of the lines can be grouped and/or redistributed across the remaining lines without delay. In this way, an uninterrupted operation of the interface means is possible even in the case of an unforeseen failure of a line.

Monitoring the usability of the lines can be based on measuring the resistance of the lines and determining that a line is usable if the resistance is lower than a predefined threshold, e.g. less than 10Ω. Similarly, a short-circuit between different lines can be determined based on the resistance between different lines. For example, it can be determined that lines are usable if the resistance between one line and each of the other lines is higher than at least 1 MΩ. In this way, not only short-circuits, but also too low-ohmic ("soft") connections between different lines can be detected as an unusable state.

It can be advantageous to provide a monitoring unit at each side of the lines such that the monitoring units can determine the resistance of the lines between them, in particular the detection of open-circuited lines. It is pointed out, however, that open-, short-circuit and resistance measurements are just examples of the tasks that the cable monitor/checker can perform.

According to another aspect of the invention, the interface means comprises a first and a second grouping and/or redistributing means, wherein the first grouping and/or redistributing means is connected to the second grouping and/or redistributing means through a cable comprising the lines and wherein the second grouping and/or redistributing means is connected to a device, preferably to a lead of a medical device.

Having a first and a second grouping and/or redistributing means makes it possible that a signal from a first connection means (which is connected to the first grouping and/or redistributing means) is distributed on a certain line and the signal is extracted from this line through the second grouping and/or redistributing means. Preferably, the first and second grouping and/or redistributing means are installed at the opposite ends of the lines.

If the first and second grouping and/or redistributing means are implemented as crosspoint switch matrix means, the first and second crosspoint switch matrix means can be controlled in the same way. For example, if the first crosspoint switch matrix means connects a certain first connecting means with row 3 (which is connected to line 3) and it is then detected that line 3 is no longer functional, the first crosspoint switch matrix means can be controlled to connect the first connecting means with row 2 instead. In this case, the second crosspoint switch matrix means can be controlled in the same way, i.e. to connect those columns with row 2 that were previously connected with row 3.

According to another aspect of the invention, the interface means further comprises a first interface controller that is configured to control the first grouping and/or redistributing means and a second interface controller that is configured to control the second grouping and/or redistributing means.

Ensuring that the first grouping and/or redistributing means is always configured in the same way as the second grouping and/or redistributing means can be achieved by communicating the configuration information of the first and second grouping and/or redistributing means over one of the lines. The configuration of the first and second grouping and/or redistributing means can be determined for example by the first interface controller and the configuration is communicated to the second interface controller. Alternatively, the first and second interface controller can jointly determine the desired configuration of the first and second grouping and/or redistributing means. In yet another alternative, the configuration is only determined based on the number of available lines wherein first and second interface controller independently determine the number of useable lines, e.g. based on a first and second cable monitor. In this alternative, it needs to be ensured that first and second cable monitor use the same parameters for determining whether a line is usable or not.

According to yet another aspect of the invention, the interface means further comprises a first and/or a second memory means, configured to store a mapping between a number of useable lines and a configuration of the first and/or second grouping and/or redistributing means wherein the first and/or second interface controller are configured to control the first and/or second grouping and/or redistributing means based on the configuration information stored in the first and/or second memory means, respectively. The first and/or second memory means can be implemented as part of the first and/or second interface controller, respectively.

Having the first and second distributing means obtain the same configuration information for the first and second grouping and/or redistributing means has the advantage that it can be ensured that first and second grouping and/or redistributing means use the same configuration without having to transmit this configuration information over the lines.

According to yet another aspect of the invention, the first interface controller is connected with an interface start-up unit that is connected with the first grouping and/or redistributing means and that is configured to provide a DC and/or AC supply voltage to at least one of the lines and/or the first interface controller is connected with a ground (GND) unit that is connected with the first grouping and/or redistributing means and that is configured to provide ground to at least one of the lines, the second interface controller is connected with a power start-up unit that is connected to the second grouping and/or redistributing means and that is configured to extract a supply voltage and/or a ground from the lines, and/or the second interface controller is further connected with a supply/ground finder unit and/or a supply finder unit that is connected to the second grouping and/or redistributing means.

In one example, the interface start-up module has two columns in the IPG ICPSM so that it can also provide ground on its own.

According to yet another aspect of the invention, the interface start-up unit, the power start-up unit and the supply/ground finder unit are configured to be active only during an interface reconfiguration period. The duration of the reconfiguration period can be determined e.g. using a timer.

According to another aspect of the invention, the interface means is an interface between a supply device, in particular an implantable pulse generator, and a medical device, in particular an active lead can of a deep brain stimulation system, wherein the first grouping and/or redistributing means is located on the supply device and the second grouping and/or redistributing means is arranged on and being a part of the medical device.

Similarly, the first interface controller can be located on the supply device and the second interface controller can be located on the medical device. In this way, signals with different specific functionalities can be transferred from the supply device to the medical device even if one of the lines fails.

Furthermore, the present invention relates to a system for neural applications with the features of claim 12. Accordingly, a system for neural applications, exemplarily a system for brain applications, especially a deep brain stimulation system is provided comprising at least one interface means according to any of claims 1 to 11.

The present invention also relates to a system for neural applications, in particular for brain applications, especially a deep brain stimulation system, comprising at least one interface means as described above with the features of claim 12.

Moreover, the present invention also relates to a method for communicating a plurality of signals, in particular power and/or data signals and/or control signals over a plurality of lines, in particular over a plurality of lines of an interface means as described above, wherein the method comprises the steps of claim 13. Accordingly, there is provided a method for communicating a plurality of signals, in particular power and/or data signals and/or control signals, over a plurality of lines, in particular over a plurality of lines of an interface means as described above, comprising the steps of detecting which lines of the plurality of lines are usable, in particular by measuring the resistance between different lines and the resistance along the lines, and configuring at least one grouping and/or redistributing means such that the plurality of signals is transferred over those lines that have been determined to be useable.

The plurality of signals can correspond to a plurality of different specific functionalities. The number of different specific functionalities can be higher than the number of lines.

According to another aspect of the invention, the plurality of lines connect a supply device, in particular an implantable pulse generator, to a medical device, in particular an active lead can, and configuring the at least one grouping and/or redistributing means comprises configuring a first grouping and/or redistributing means located on the supply device and configuring a second grouping and/or redistributing means located on the medical device.

According to another aspect of the invention, the method comprises a step of detecting which of the lines are configured to supply power and ground. In particular, this step can be performed after detecting which of the lines are usable and before configuring a grouping and/or redistributing means.

According to another aspect of the invention, the method further comprises a step of performing time-division multiplexing to transport several signals over a single line.

Performing time-division multiplexing has the advantage that several signals can be communicated over the same line without losing information. Different methods of time-division multiplexing that are known to the skilled person can be used in this context.

Figure 2:
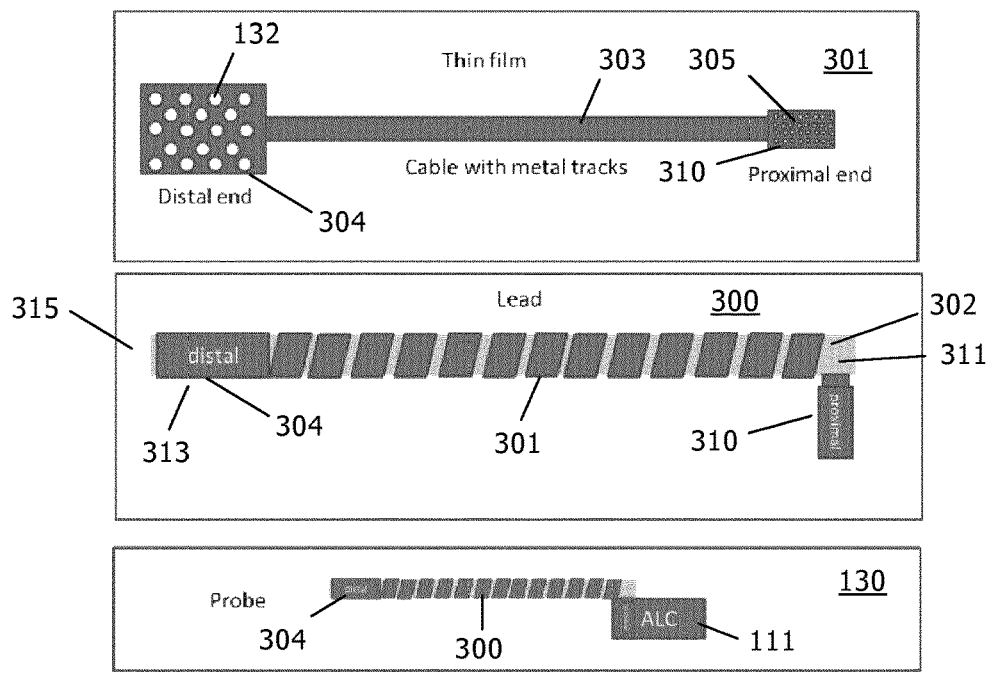
Figure 3:
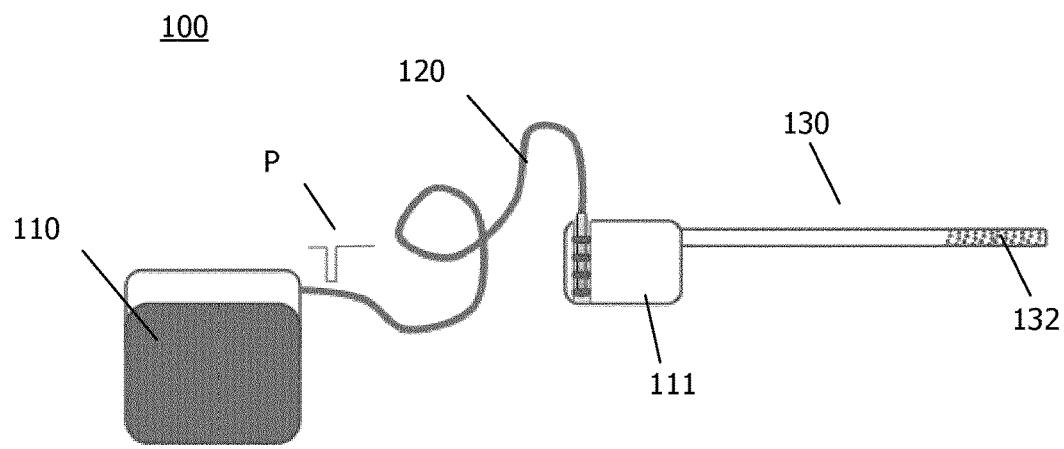
Figure 4:
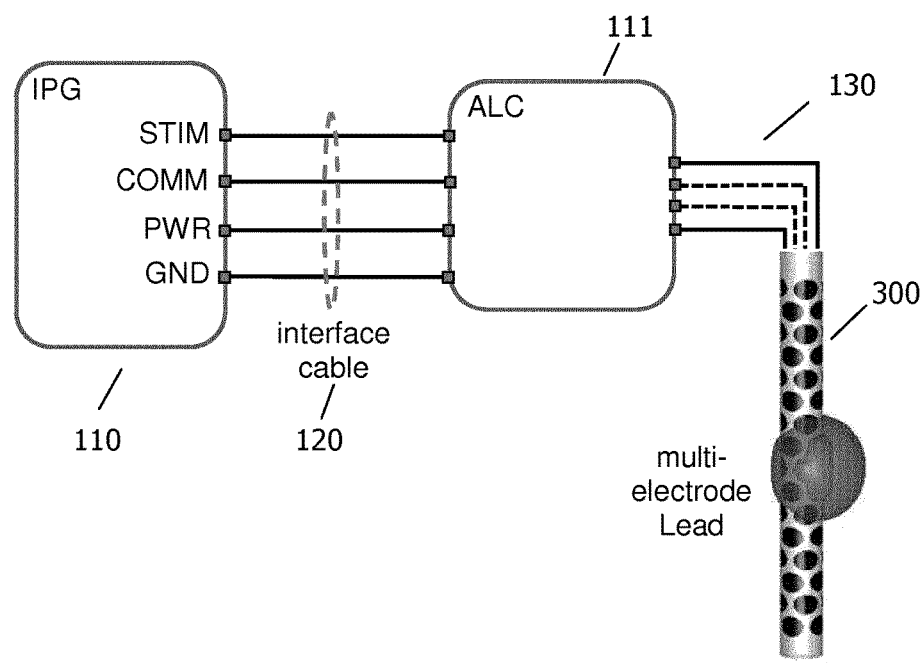
Figure 5:
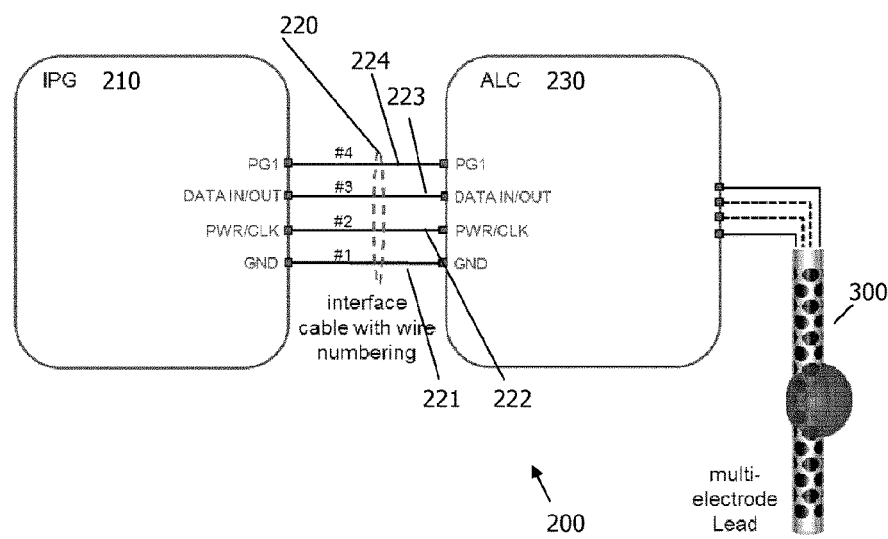
Figure 6:
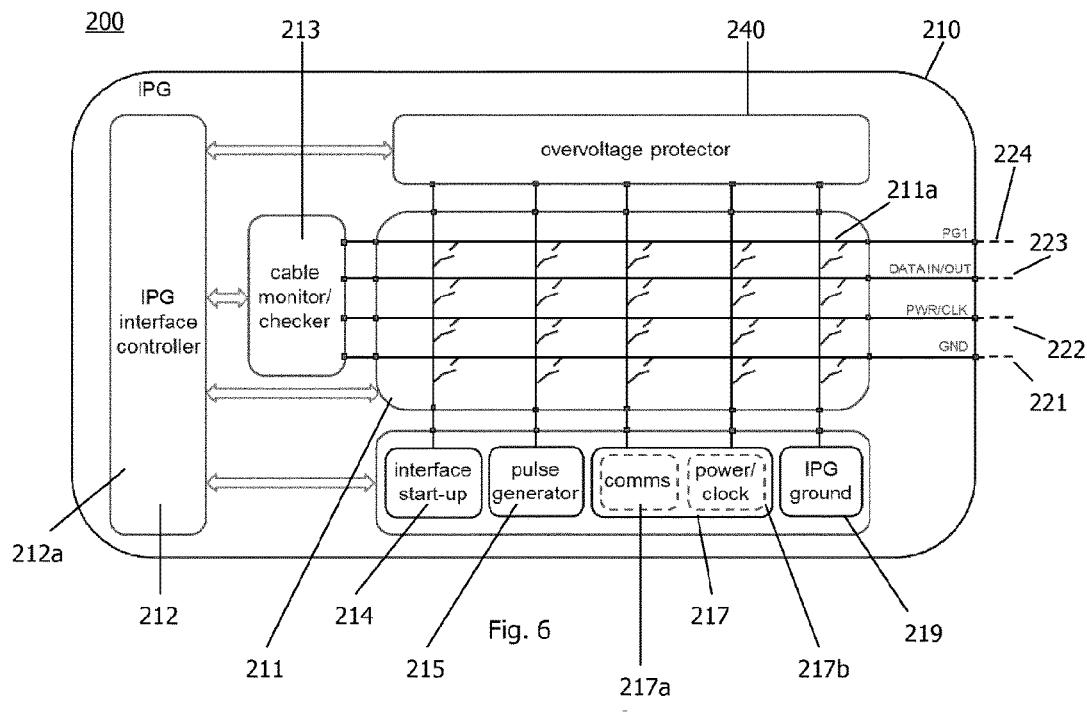
Figure 7:
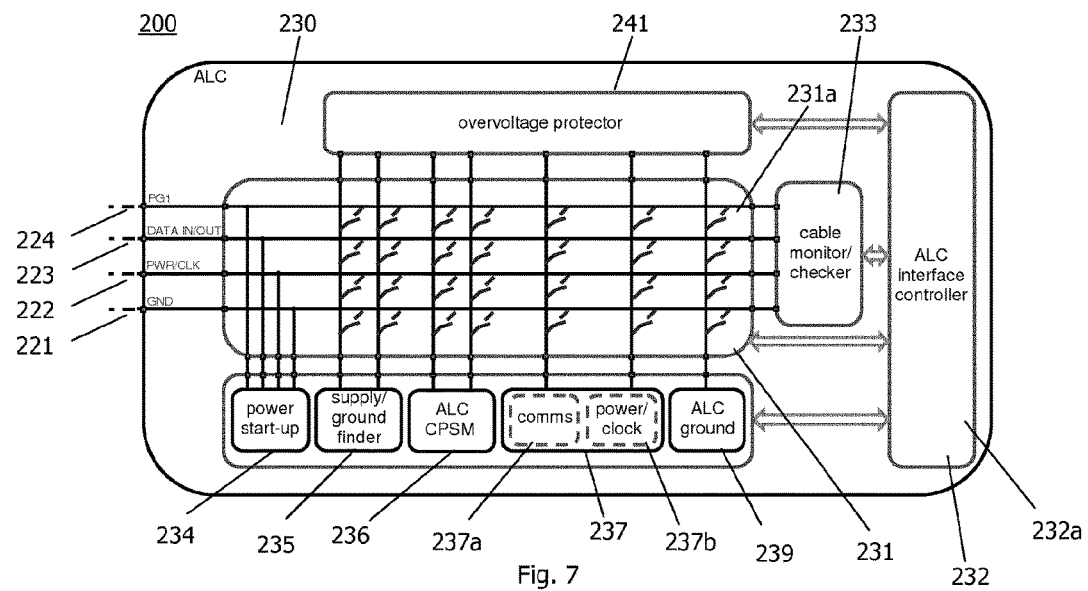
Figure 8A:
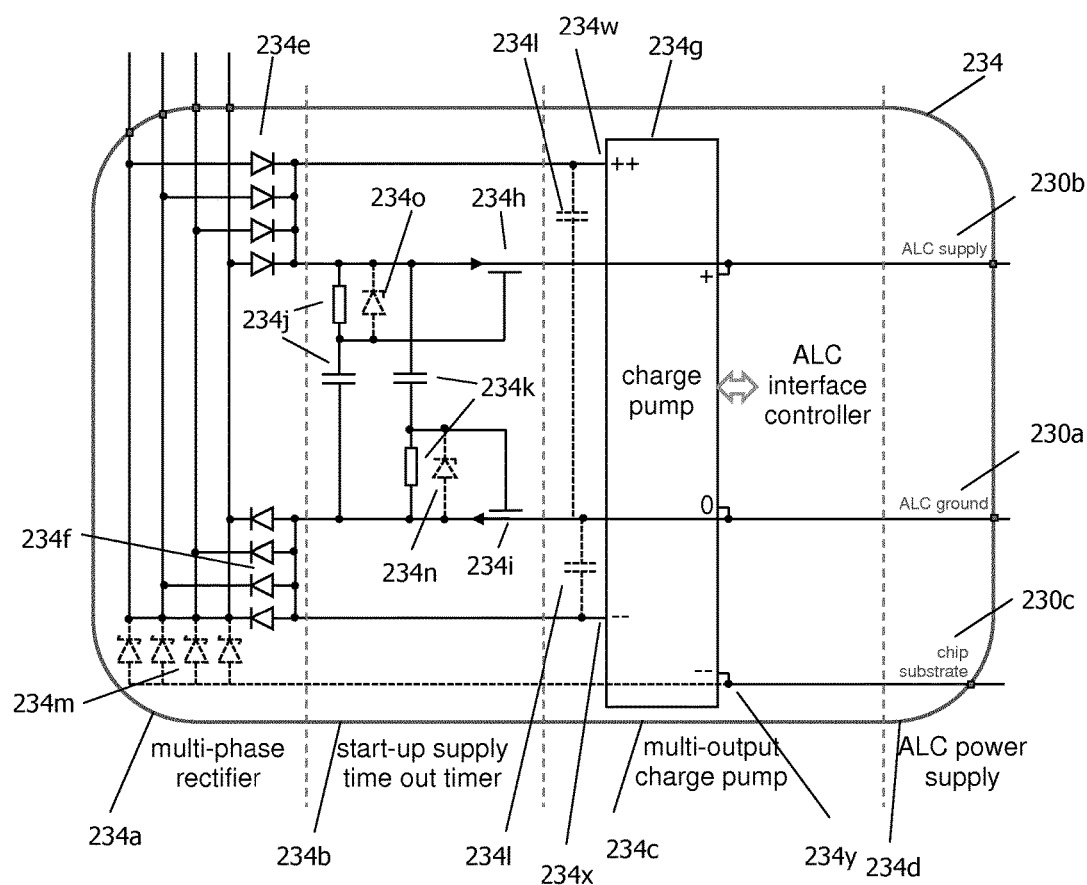
Figure 8B:
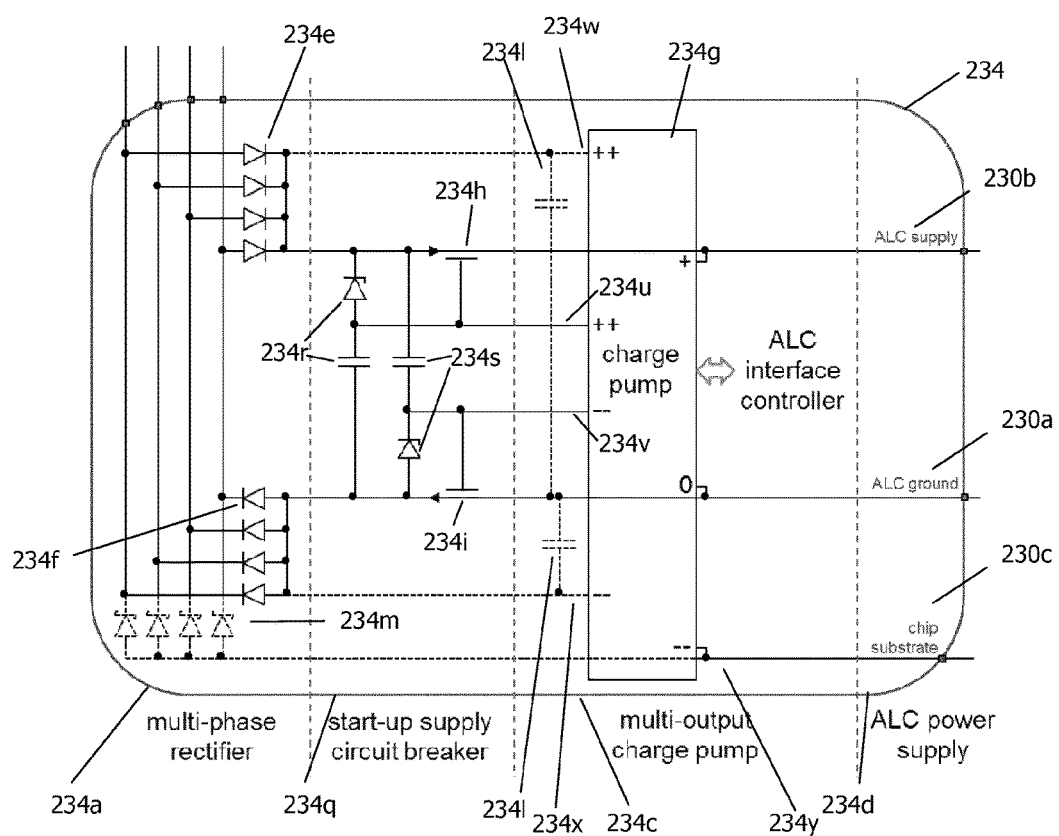
Figure 9:
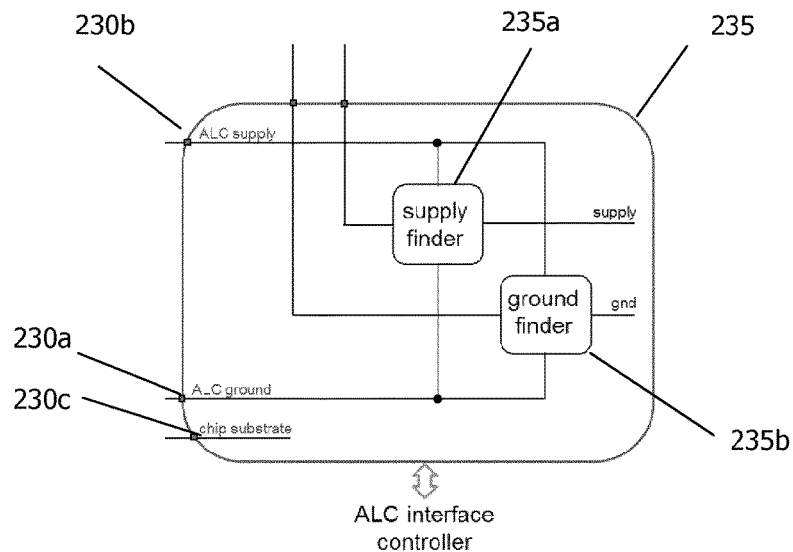
Figure 10:
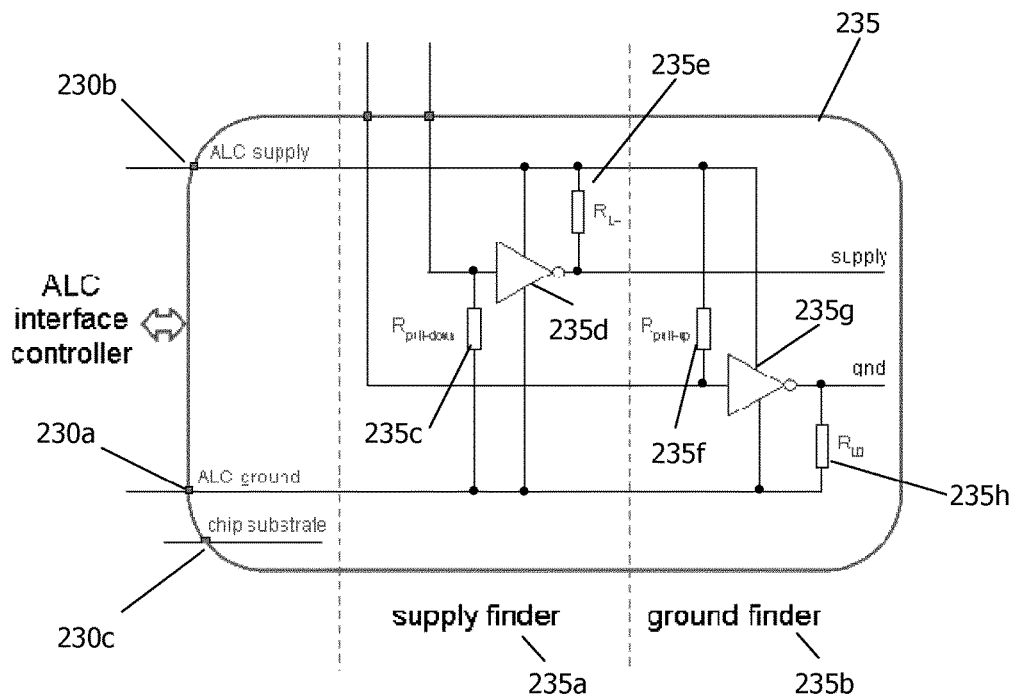
Figure 11:
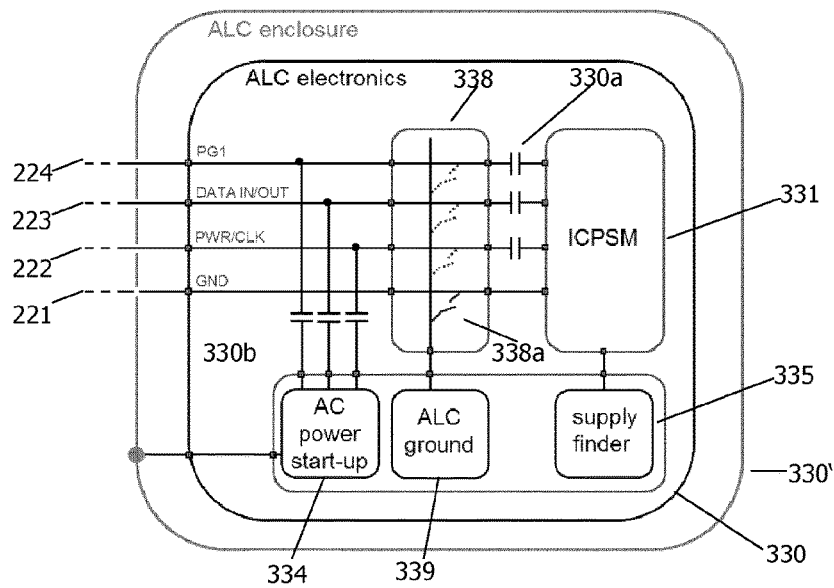
Figure 12:
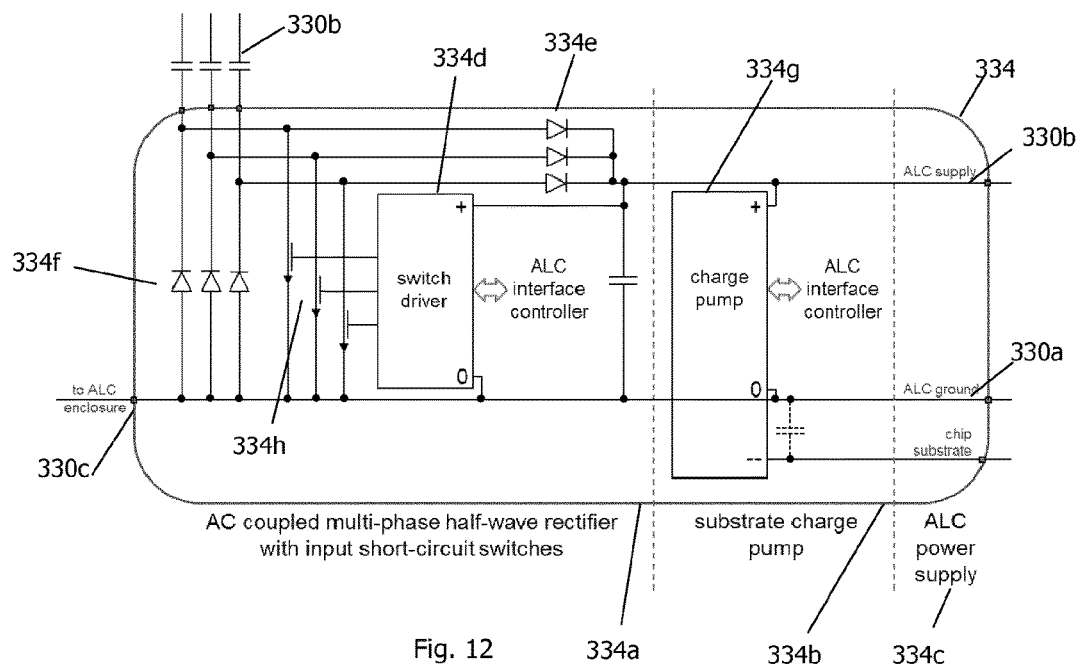

Further details and advantages of the present invention shall be described hereinafter with respect to the drawings:

FIG. 1: a schematic drawing of a neurostimulation system for deep brain stimulation (DBS);

FIG. 2: a further schematic drawing of an active lead neurostimulation system for deep brain stimulation (DBS) and its components;

FIG. 3: a schematic drawing of a probe system according to the present invention;

FIG. 4: a schematic drawing of a modular neural stimulator;

FIG. 5: a schematic drawing of a modular neural stimulator with an interface means according to the present invention;

FIG. 6: a schematic drawing of one side of an interface means according to the present invention;

FIG. 7: a schematic drawing of the corresponding second side of an interface means according to the present invention;

FIG. 8a: a schematic circuit diagram of a power start-up block of an interface means according to the present invention;

FIG. 8b: a schematic circuit diagram of a power start-up block of another interface means according to the present invention;

FIG. 9: a schematic drawing of a supply/ground finder unit according to the present invention;

FIG. 10: a schematic circuit diagram of a supply/ground finder unit according to the present invention;

FIG. 11: a schematic circuit diagram of ALC electronics of an interface means according to the present invention; and FIG. 12: a schematic diagram of a modified power start-up module of an interface means according to the present invention.

A possible embodiment of a neurostimulation system 100 for deep brain stimulation (DBS) is shown in FIG. 1. The neurostimulation system 100 comprises at least a controller 110 that may be surgically implanted in the chest region of a patient 1, typically below the clavicle or in the abdominal region of a patient 1. The controller 110 can be adapted to supply the necessary voltage pulses. The typical DBS system 100 may further include an extension wire 120 connected to the controller 110 and running subcutaneously to the skull, preferably along the neck, where it terminates in a connector. A DBS lead arrangement 130 may be implanted in the brain tissue, e.g. through a burr-hole in the skull.

FIG. 2 further illustrates a typical architecture for a Deep Brain Stimulation probe 130 that comprises a DBS lead 300 and an Active Lead Can (ALC) element 111 comprising electronic means to address electrodes 132 on the distal end 304 of the thin film 301, which is arranged at the distal end 313 and next to the distal tip 315 of the DBS lead 300. The lead 300 comprises a carrier 302 for a thin film 301, said carrier 302 providing the mechanical configuration of the DBS lead 300 and the thin film 301. The thin film 301 may include at least one electrically conductive layer, preferably made of a biocompatible material. The thin film 301 is assembled to the carrier 302 and further processed to constitute the lead element 300. The thin film 301 for a lead is preferably formed by a thin film product having a distal end 304, a cable 303 with metal tracks and a proximal end 310. The proximal end 310 of the thin film 301 arranged at the proximal end 311 of the lead 300 is electrically connected to the ALC element 111. The ALC element 111 comprises the switch matrix of the DBS steering electronics. The distal end 304 comprises the electrodes 132 for the brain stimulation. The proximal end 310 comprises the interconnect contacts 305 for each metal line in the cable 303. The cable 303 comprises metal lines (not shown) to connect each distal electrodes 132 to a designated proximal contact 305.

FIG. 3 shows schematically and in greater detail an embodiment of a system 100 for brain applications, here for neurostimulation and/or neurorecording as a deep brain stimulation system 100 as shown in FIGS. 1 and 2. The probe system 100 comprises at least one probe 130 for brain applications with stimulation and/or recording electrodes 132, whereby e.g. 64 electrodes 132 can be provided on outer body surface at the distal end of the probe 130. By means of the extension wire 120 pulses P supplied by controller 110 can be transmitted to the ALC 111. The controller 110 can be an implantable pulse generator (IPG) 110.

FIG. 4 exemplarily shows a schematic drawing of a possible embodiment of a modular neural stimulator composed of two modules according to the present invention: an IPG (Implantable Pulse Generator) 110 and an ALC (Active Lead Can) 111 with a 4-wired interface cable 120 between them. It is understood that there may also be more or fewer wires provided when carrying out the invention.

In the modular deep brain stimulator, a 4-wired interface cable between the IPG and the ALC can provide stimulation pulses (STIM) via the ALC to a multi-electrode Lead, a communication channel (COMM) between IPG and ALC, power (PWR) to the ALC and grounding (GND).

If one of the four wires (in other embodiments one or more of the plurality of wires) of the interface cable between the IPG and the ALC fails (for example due to shorts or opens) or otherwise becomes electronically unusable (for example due to increased resistivity, degrading isolation, contact with the body etc.), the complete implant might fail and/or has to be switched off or put in another harmless state in which stimulation of the patient is stopped. Thus the interface cable is literally the weakest link of a modular implant. This can be circumvented by using an interface means according to the present invention.

FIGS. 5 to 10 show components of interface means according to one possible embodiment of the present invention, whereby the interface means are used as part of a modular deep brain stimulator.

High-Level Operating Mechanism

FIG. 5 illustrates the high-level operating mechanism of an interface means 200 according to the present invention. The IPG side 210 of the interface means is integrated into an IPG and the ALC side 230 is integrated into the ALC. In the following, the IPG side 210 will be referred to as IPG 210 and the ALC side 230 will be referred to as ALC 230. The complete system as indicated in FIG. 5 represents a modular deep brain stimulator whose interface cable 220 contains four wires 221, 222, 223, 224. Experiments have shown this number of wires to be the optimum solution in the design space of the wired interface for this implant. The setup of IPG 210, ALC 230 and multi-electrode lead 300 is comparable to the setup shown in FIG. 4, however, the functionalities of the wires can be dynamically changed.

The physical wires of the interface are numbered from #1 to #4, while the interface function of each wire is displayed at each in- and/or output pin of IPG 210 and ALC 230 for the initial situation in which all interface cable wires are applied to establish the interface between IPG 210 and ALC 230. As can be seen in FIG. 5, wire #1 221 is preconfigured to be used for ground (GND), wire #2 222 is preconfigured to be used for power transmission and clock signal (PWR/CLK), wire #3 223 is preconfigured to be used for data input and output (DATA IN/OUT), and wire #4 224 is preconfigured to be used for pulse generation (PG1).

Both the IPG 210 and ALC 230 contain (electronic) means to (re)configure the interface between them and the high-level operating mechanism of this (re)configurable interface is based on 3 fundamentals:

1. If one of the wires of the interface cable, which comprises the four wires 221, 222, 223, 224, becomes unusable, the routing of the interface signals is redistributed across the remaining cable wires. This rerouting of signals is done by means of a cross-point switch matrix 211, 231 on both sides of the interface cable 220 i.e. a switch matrix in both the IPG 210 and ALC 230. Simultaneously, the proper adjustment of the IPG 210 and ALC 230 electronics responsible for generating and processing the interface signals can be necessary because of a change in interface protocol or the available signals on an interface wire due to the rerouting.
2. The trigger for rerouting is the detection of a fault or undesired condition on one or more wires of the interface cable. A fault can for example be a detected broken wire or a short between two interface wires, while an example of an undesired condition might be a (significant) increase in wire resistance leading to extra power consumption to get the desired signal across. Thus electronics must be added that monitors the condition of the physical interface and raises a flag when a fault or an undesired condition is encountered.

The IPG 210 regularly checks to see if a stimulation line voltage or current does not exceed a predefined range and an error is issued if it does and the stimulation is stopped. The interface cable monitor can be seen as an extension of this rudimentary diagnostics.

3. Finally, one has to define an interface (re)configurability protocol that predefines how the rerouting and adaptation of the interface protocol in normal operation is done depending on the type of detected physical interface fault or undesired condition. Thus a flag raised by the interface cable monitor, or any other module of the interface electronics, sets in motion a predefined rerouting of desired signals and, if necessary, a change in the interface protocol.

Examples of flags that the cable monitor can raise are "short between wires #1 and #3", an "open on wire #2" or "resistance too high on wire #4" or a combination of these, for example, "open on wire #2 and resistance too high on wire #2". A raised flag basically signals that one or more interface wires might be lost and one can predefine the (re)routing, the desired interface signals and the corresponding interface protocol based on the number of remaining interface wires left.

Note that a selection of the interface signals enables a graceful degradation of the interface if it is not possible, for technical or physical reasons, to map all signals on the remaining interface wires anymore.

The link between the number of remaining wires and the interface configuration (interface signals, assignment to wires, interface protocol) can be stored in memory means which are provided both at the IPG 210 and at the ALC 230 so that both modules only have to know what the remaining number of interface wires is to (re)configure the interface accordingly and identically.

Note that some flags raised by the cable monitor require additional checking. For example, if the flag "resistance too high on wire #2" is raised, it might be because interface wire #2 is broken or, for example, that some connections to the previously connected Lead electrodes are broken. Obviously, if the latter is the case, no changes to the IPG-ALC interface are needed, although an error or warning message might be issued by the IPG 210.

High-Level IPG Interface Architecture

The (re)configurable interface architecture of the interface means 200 according to the present invention is composed of two parts that communicate with each other via the interface cable 220. The high-level interface architecture on the IPG 210 side is shown in FIG. 6. Its core is the grouping and switching means, i.e. here the first grouping and/or redistributing means 211, which is realized as an interface cross-point switch matrix (ICPSM) 211 in the middle, that does the actual physical (re)routing of signals across the (available) interface wires 221, 222, 223, 224. The ICPSM switches 211a can be (floating) high-voltage current bidirectional switches as e.g. described in WO2011128809 A2 depending on if the switches 211a need to be continuously on (e.g. for connecting ground) or not (e.g. duty-cycled stimulation pulses), respectively.

The interface wires 221, 222, 223, 224 form the rows of the ICPSM 211 and are connected to the cable monitor/checker 213 shown in the left hand side of FIG. 6. The columns are attached to the interface electronics itself shown in the bottom part of FIG. 6. The IPG interface controller 212 as a first interface controller 212 at least communicates with the cable monitor/checker 213, the interface start-up unit 214, the pulse generator 215, the electronics responsible for communication 217a and for power and clock generation 217b and the overvoltage protector 240.

The most right column is connected to IPG ground 219. The electronics responsible for data communication ("comms") 217a and power and clock generation ("power/clock") 217b is a single (re)configurable block 217 connected to two ICPSM columns. The stimulation pulse generator output 215 is connected to another column in the ICPSM.

The most left column is connected to the interface start-up circuit 214 which forms the interface start-up unit 214. This circuit is only used when the interface needs to be (re)configured and is not an active part of the interface electronics once the interface is in normal operation (again).

All columns are also connected to a (programmable) overvoltage protection circuit 240 shown at the top of FIG. 6. It makes sure that the voltage on a column never exceeds a (programmable) value so that the connected electronics can never be damaged by too high voltages. For example, if the pulse generator line (PG1, wire #4 224) is shorted to the communications line (DATA IN/OUT, wire #3 223) due to a fault condition, the high stimulation voltages of the pulse generator 215 might damage the sensitive low-voltage electronics of the communication circuitry if no appropriate protection were present on the columns of the ICPSM 211.

The control over the complete interface on the IPG 210 side is in the hands of the IPG 210 interface controller on the left hand side of FIG. 6. It communicates with all the interface electronics including the ICPSM 211 of the IPG 210.

Initially, when the interface means 220 is fully functional, the bottom wire #1 221 carries the mutual ground of IPG 210 and ALC 230, followed by the power and clock signals on wire #2 222, the communication line on wire #3 223 and stimulation pulse generator output on the top wire #4 224.

High-Level ALC Interface Architecture

FIG. 7 shows the high-level interface architecture on the ALC 230 side of the interface means 200, including an ALC interface controller 232 as a second interface controller 232, a cable monitor/checker 233 and another interface cross-point switch matrix (ICPSM) 231, i.e. the second grouping and/or redistributing means 231, for signal (re)routing. As can be seen in FIG. 7, the high-level interface architecture on the ALC side is similar to the one on the IPG side: the core is another interface cross-point switch matrix (ICPSM) 231. The difference in functionality between the interface architecture on IPG and ALC side lies in the power start-up 234, supply/ground finder 235 and ALC cross-point switch matrix (CPSM) 236 blocks. Also indicated in FIG. 7 are the ends of the wires 221, 222, 223, 224 that connect the ALC 230 with the IPG 210.

The ALC CPSM block 236 should not be mistaken for the ICPSM 231 of the ALC interface architecture. The ALC CPSM 236 connects a desired set of lead electrodes to its column(s) in the ICPSM 231 of the ALC 230. One column can (dynamically) be connected to the pulse generator line 224 of the interface cable 220, and, if desired, the other column can (simultaneously) be used to connect a (different) set of Lead electrodes to ALC ground 239. In this way, stimulation pulses from the IPG 210 can be delivered via a desired set of electrodes to a specific target in the brains.

Similar to the configuration of the IPG side 210, the most right column is connected to ALC ground 239. The electronics responsible for data communication ("comms") 237a and power and clock generation ("power/clock") 237b is a single (re)configurable block 237 connected to two ICPSM columns. Each column of the ICPSM 231 is connected to the overvoltage protector 241. Columns and rows of the ICPSM 231 are connectable via switches 231a.

The power start-up block 234 forming the power start-up unit 234 and the supply/ground finder 235 forming the supply/ground finder unit 235 are only active when the wired interface is (re)configured and they interact with the interface start-up block 214 on the IPG 210 side during this reconfiguration period. The power start-up block 234 delivers power to the ALC 230 when the interface is (re)configured and the supply/ground finder 235 establishes which lines of the wired interface are used by the IPG 210 to supply power and ground to the ALC 230. The supply/ground finder 235 can also be used by the ALC 230 interface controller to find out how many interface wires are available to set-up the interface.

Once the ALC 230 has established the number of available interface wires, it retrieves the stored interface configuration (interface signals, assignment to wires, protocol) from a (non-volatile) memory means and configures the ALC side of the interface accordingly. The same is done at the IPG 210 side except that there is no need to re-establish power because the IPG 210 electronics is permanently connected to the battery of the IPG 210.

ALC Power Start-Up Protocol and Implementation

The first thing that needs to be done during the interface set-up process is the restoration of power to the ALC 230, because otherwise no actions can take place at the ALC 230 side at all. If there is no power at the ALC 230 side, all its ICPSM switches 231a of ICPSM 231 are non-conducting (open) and if the ICPSM 231 of the IPG 210 is put in the same state, all interface wires are basically floating.

Firstly, the cable monitor/checker 213 on the IPG 210 side checks if there are no shorts/low-ohmic connections between the wires of the interface cable 220. This can be realized with circuitry known to a man skilled in the art of electronics. If a short or too low-ohmic connection is found, the according pair of wires is treated as a single wire in the future in which case the number of available interface wires reduces with one.

For now, it is assumed that all wires 221, 222, 223, 224 are available to set-up the interface between IPG 210 and ALC 230 i.e. no shorts/low-ohmic connections are found. This is a reasonable assumption that should be guaranteed by the quality control process in place for the interface cable 220. Moreover, as explained later, it does not matter if one already starts with a faulty interface cable 220 or not.

The interface start-up circuit in the IPG 210 puts a DC supply voltage on one of the interface lines, for example, the PWR/CLK line (wire #2 222) to provide power to the ALC 230. Another line, for example, the GND line (wire #1 221) is connected to IPG ground. This is done by programming the ICPSM 211 via the IPG interface controller 212 accordingly.

It does not matter which two interface wires are chosen by the IPG 210 to apply (temporary) power and ground as long as they are not shorted. The applied DC voltage on a pair of interface wires is used by the power start-up circuit of the ALC 230 during the interface initiation and (re)configuration process.

The ALC power start-up circuit 234 is permanently connected to all wires 221, 222, 223, 224 of the interface cable 220 as is also shown in FIG. 7. The start-up circuit 234 is composed of a multi-phase rectifier 234a followed by a start-up supply time out timer 234b that connects directly to the ALC supply line 230b and the ALC ground line 230a as depicted in FIG. 8a. The rectifier diodes 234e prevent a direct connection (short) between the individual lines of the interface cable 220.

FIG. 8a shows the ALC power start-up circuit 234 applied during the interface initiation and (re)configuration process to supply power to the ALC 230 temporarily until the interface means 200 is restored.

The start-up supply time out timer 234b connects the multi-phase diode rectifier 234a to the ALC ground and supply lines 230a, 230b only temporarily: sufficiently long to set-up the interface link. The ALC supply line 230b is connected via a high-voltage PMOS transistor/switch 234h to the cathodes of the (top) multi-phase rectifier diodes 234e, while the ALC ground line is connected via a high-voltage NMOS transistor/switch to the anodes of the (bottom) rectifier diodes 234f. The gate of each MOS transistor 234h, 234i is connected to a simple first-order R-C circuit 234j, 234k, respectively. When power is applied to the ALC 230, the time constant of the passive R-C circuits 234j, 234k determines how long the P- and N-type MOS transistors (MOST) switches 234h, 234i are conducting.

If the power start-up circuit 234 is integrated on-chip, the capacitors might require external components to realize the needed timeout time (constants) to keep the ALC 230 supplied with power during the interface initiation and (re)configuration process. Other options to only temporarily connect the multi-phase rectifier to the ALC ground and supply lines 230a, 230b are possible. For example, a start-up supply circuit breaker 234q can be realized between the multi-phase rectifier 234a and the ALC supply line 230b and ALC ground line 230a by replacing the passive R-C networks 234j, 234k shown in FIG. 8a with (Zener) diode-C circuits 234r, 234s as shown in FIG. 8b, or (Zener) diode-R circuits (not shown).

The two (additional) charge pump outputs 234u, 234v to the gates of the P- and NMOS transistors 234h, 234i, respectively, which implement the circuit breaker functionality of the ALC power startup circuit 234 shown in FIG. 8b, are (also) under control of the ALC interface controller 232. When the controller 232 enables these two pump outputs 234u, 234v, the circuit breaker 234q is activated, because the MOS transistors 234h, 234i connecting the multi-phase rectifier 234a with the ALC supply and ground lines 230b, 230a become non-conducting i.e. are opened.

If the ALC controller 232 does not activate the two pump outputs 234u, 234v, leakage currents to the capacitors of the (Zener) diode-C circuits 234r, 234s determine the time out time of the circuit breaker 234q. This time out time can be relatively long, even when the capacitors are integrated on-chip, because on-chip leakage currents can be extremely small, especially at the relatively low human body temperature. Thus in practice, the ALC controller 232 activates the circuit breaker 234q.

Note that when the circuit breaker is activated by the ALC interface controller 232, the (Zener) diodes are eventually forward biased and pull the upper 234e and lower 234f set of rectifier diodes to a (sufficiently) high positive and negative bias voltage, respectively. Therefore, the (most upper and lower) high-voltage charge pump outputs 234w, 234x that directly connect to the two sets of rectifier diodes 234e, 234f, respectively, can be omitted if desired.

The now available DC voltage on the ALC supply lines 230b is used as wake-up signal for the ALC interface controller 232 (not shown in FIGS. 8a, 8b). It immediately starts to query the supply/ground finder module 235 of the ALC interface electronics 230 shown in FIG. 9. This module contains a supply finder submodule 235a and a ground finder submodule 235b and each has a dedicated column in the ICPSM 231 of the ALC 230. These submodules, as well as all the other ALC interface electronics 230 are powered via the ALC ground and supply lines 230a, 230b.

The common substrate terminal, only present if the (interface) electronics is (partly) integrated on-chip, is also shown separately in FIG. 9. The chip substrate 230c is biased via the charge pump 234g of the power start-up module 234 of the ALC 230. The available DC voltage on the ALC supply lines is also used to wake-up this charge pump 234g. It immediately enables the negative high-voltage output 234y connected to the chip substrate to bias it at a sufficiently low voltage. The other outputs of the charge pump 234g remain disabled and high-ohmic. Note that if the chip substrate is not of the p-type but of the n-type, a sufficiently high positive bias voltage is needed to bias the chip substrate correctly.

FIGS. 8a and 8b also show the multi-output charge pump 234c of the power start-up block 243.

FIG. 9 shows the supply/ground finder module 235. The ALC interface controller 232 starts by connecting, one-by-one, each wire 221, 222, 223, 224 of the interface cable 220 to the supply finder 235a and subsequently the same procedure is carried for the ground finder 235b. A 'low' voltage near the ALC ground level on the binary digital output line labelled supply or a 'high' voltage near the ALC supply level on the binary digital output line labelled gnd indicates that the scanned interface wire is connected to the (temporary) supply voltage or (permanent) ground of the IPG 210, respectively. This signalling is achieved by the implementation of the supply/ground finder module 235 as shown in FIG. 10.

The supply/ground finder module 235 is also connected to the chip substrate 230c, the ALC ground 230a and the ALC supply 230b.

FIG. 10 shows an implementation of the supply/ground finder 235 by means of two inverters 235d, 235g and a set of pull-up/down resistors 235c, 235f at their input and a set of load resistors 235e, 235h at their output.

If the supply finder submodule 235a is not connected to a wire 221, 222, 223, 224 of the interface cable 220, the pull-down resistor $R_{pull-down}$ 235c at the input of its inverter 235d keeps its binary output signal supply near the ALC supply level 230b and no current is drawn by the supply finder submodule 235a from the ALC supply 230b. If the ALC interface controller 232 connects the supply finder submodule 235a to an interface cable wire 221, 222, 223, 224 that is not connected, there is no change in the supply output signal. The same is true if the line is connected to IPG ground. However, if the line carries the DC supply voltage put on it by the interface start-up module in the IPG 210, the inverter 235d changes state and the voltage on its digital output line labelled supply becomes close to ALC 230 ground.

The appearing voltage drop across the (programmable) resistive $R_{L+}$ load 235e, when the supply finder submodule is connected to an interface wire with the supply voltage on it, leads to an additional current drawn from the ALC 230 supply, and therefore, the current provided by the IPG start-up circuit 214 increases. If the RL+ load resistance 235e is chosen sufficiently small, this sudden increase in current drawn from the IPG interface start-up module 214 can easily be detected by this module. This form of load modulation can therefore be used to signal to the IPG interface controller 212 that the ALC 230 has found the supply line of the interface cable 220, while the ALC controller 232 can signal this by the low voltage on the digital output line of the supply finder submodule 235a.

The operation of the ground finder submodule 235b is basically the same but the signals on its ground output line are the opposite. Thus if its input is connected to an interface line that is not connected, its input pull-up resistance $R_{pull-down}$ keeps its output line voltage gnd unchanged and close to ALC ground 230a. The same is true if the interface wire turns out to be connected to the IPG interface start-up module 214. However, if the interface wire is connected to IPG ground, the inverter 235g of the ground finder submodule 235b changes state and its digital output signal ground becomes close to the voltage of the ALC supply line 230b.

The appearing voltage drop across the (programmable) resistive $R_{LO}$ load 235h, when the ground finder submodule 235b is connected to a grounded interface wire, leads to an additional current drawn from the ALC supply 230b, and therefore, the current provided by the IPG start-up circuit 214 increases. If the $R_{LO}$ load resistance 235h is chosen sufficiently small, and sufficiently different in value with respect to the $R_{L+}$ load 235e of the supply finder submodule 235a, this sudden and different change in current drawn from the IPG interface start-up module 234 can easily be detected by this module again. This load modulation can be used to signal to the IPG interface controller 212 that the ALC 230 has found the (permanent) interface cable ground line, while the ALC controller 232 can signal this by the high voltage on the digital output line of the ground finder submodule 235b.

Once the ALC interface controller 232 knows which line or lines, in case of a short between interface wires, carry the (temporary) start-up supply voltage and (permanent) ground provided by the IPG 210, it connects the identified ground wire to the ALC ground module 239 permanently i.e. it connects the found cable wire(s) to the ALC ground line 230a, while the found supply voltage line(s) are connected to the ALC communication and power/clock module 237, and on command of the ALC interface controller 232, internally with the power/clock submodule 237b. Next, the communication and power/clock module 237 is enabled by the ALC interface controller 232 so that this module can put the appropriate DC voltage on the ALC supply line 230b. Finally, the ALC interface controller 232 applies (another unique form of) load modulation on the ALC supply line(s) to notify the IPG 210 that (permanent) power to the ALC 230 has been restored.

The moment that the ALC ICPSM 231 is configured to provide power via the ALC communication and power/clock module 237, the multi-phase diode rectifier 234a can be disconnected from the ALC ground and supply lines 230a, 230b. In the ALC power start-up circuit shown in FIG. 8a, the start-up supply time out timer circuit 234b disconnects the rectifier from the ALC ground and supply lines 230a, 230b automatically. In the ALC power start-up circuit 234 shown in FIG. 8b, the MOST switches of the start-up supply circuit breaker 234q can actively be made non-conductive (opened) on command of the ALC interface controller 232.

The high-voltage charge pump outputs 234w, 234x and/or 234u, 234v that provide a positive bias voltage to the upper set of multi-phase rectifier diodes 234e and a negative bias voltage to the lower set of multi-phase rectifier diodes 234f are designed to be (sufficiently) larger than the largest positive and (sufficiently) smaller than the largest negative voltage every appearing on the interface wires, respectively. In this way, all the diodes of the multi-phase rectifier get and remain reversed biased during normal interface operation, and therefore, the start-up supply time out timer 234b or circuit breaker 234q is effectively decoupled from the interface cable 220 once the start-up supply charge pump 234g is fully enabled by the ALC interface controller 232.

The outputs 234w, 234x and/or 234u, 234v of the charge pump 234 that provide the bias voltage for the multi-phase rectifier diodes 234e, 234f must have a sufficiently low output impedance so that the rectifier diodes 234e, 234f remain reversed biased and the power start-up circuit remains decoupled from the interface cable when the interface is fully operational. The addition of reservoir capacitors 234l between the high-voltage charge pump outputs connected to the rectifier diodes 234e, 234f and ALC ground 230a can help in this respect. This is shown by the dashed capacitors 234l in FIGS. 8a and 8b. In addition, Zener diodes 234n, 234o, explicitly shown as dashed diodes 234n, 234o in FIG. 8a, or any other voltage limiting means, may be put across the gate-source terminals of low-voltage driven MOS transistors 234h, 234i to prevent that the high-voltage MOS switches 234h, 234i of the start-up supply time out timer 234b and circuit breaker 234q can accidently be damaged.

The chip substrate voltage is only well defined after the charge pump 234g is woken up. If this turns out to be a problem (external) Schottky diodes 234m can be applied as shown by the dashed set of Schottky diodes connected between the chip substrate/charge pump output terminal and the cathodes of the lower set of rectifier diodes 234f. This guarantees that (on-chip) substrate diodes remain reversed biased during the wake-up process of the charge pump 234g.

Instead of a charge pump other voltage conversion (boosting) means can be applied to provide the needed bias voltages to decouple the power start-up circuit from the interface cable. Also note that in normal operation, when the power start-up module 234 is effectively off-line, both DC and AC signals can be applied on the interface cable 220, for example, AC stimulation pulses.

Finally note that if desired, various switches can be added to the ALC power start-up module 234 that actively discharge the applied capacitors when it is detected that power to the ALC 230 is (about to get) lost. Otherwise, the inherent (chip) leakage currents eventually discharge all capacitors.
Detection of Available Interface Wires At this point, power is permanently available to the ALC 230 and the actual interface can be built-up based on the pre-agreed i.e. stored interface configuration (interface signals, assignment to wires and interface protocol) stored e.g. in first and second (non-volatile) memory means 212a, 232a. The first memory means 212a is implemented as part of the IPG interface controller 212, the second memory means 232a is implemented as part of the ALC interface controller 232. The chosen interface configuration depends on the available number of interface wires, and therefore, both the ALC 230 and the IPG 210 have to find and acknowledge to each other each interface cable wire that is available for the interface and as a result also the total number of wires that can be applied to build-up the interface.

There are many ways for both the IPG 210 and ALC 230 to detect which interface wires, besides the ones already used to supply power, are available to build-up the interface link. For example, the interface start-up module of the IPG 210 can put a DC or AC voltage on the remaining interface wires and the ALC cable monitor/checker 233 can acknowledge to the IPG with load modulation that it has detected the applied voltage. If no acknowledgement is received on an interface wire by the IPG 210 in time, it is communicated to the IPG interface controller 212 that this interface line cannot be used for the interface because of an apparent broken (open-circuited) line. On the ALC side, if the ALC cable monitor/checker doesn't detect a voltage on an interface wire, it assumes that this interface wire is broken.

After detection of each available interface wire, and therefore, the number of available interface wires, the IPG 210 and ALC 230 can restore the interface based on the pre-agreed stored relation between available number of interface wires and interface configuration.

IPG-ALC Interface Restoration

Although the IPG interface start-up circuit 214 and IPG ground 219 can be connected to any of the available interface wires at the start of the interface (re)configuration process, one could pre-agree that IPG ground 219 is connected to the available wire with the lowest interface wire number (in our example, this is wire number #1 221 if the interface is fully intact) and that the interface start-up circuit 214 is connected to the next available wire with the lowest interface wire number (in our example, this is wire #2 222).

Thus during the ALC power restoration process, ALC ground module 239, and therefore ALC ground line 230a, is connected to wire #1 221 and the power/clock part 237b of the ALC communication and power/clock module 237 is connected to wire #2 222, and therefore, to the IPG interface start-up circuit 214. After restoration of power to the ALC 230, the IPG interface start-up circuit 214 is disconnected and line #2 222 is connected to the power/clock submodule 217b of the IPG communication and power/clock module 217 in such a way that power is maintained to the ALC 230, for example, via a make-before-break of the related IPG ICPSM switches 211a to establish an uninterrupted ALC power supply. Next, the IPG power/clock submodule 217b is enabled and the interface start-up module 214 is disabled by the IPG interface controller 212 which is subsequently detected by the ALC power/clock submodule 237b and/or ALC cable monitor/checker 233.

In a similar manner is the communication between the IPG 210 and ALC 230 brought back on-line on wire #3 223 which leaves the last wire #4 224 for pulse generation. Once communication is restored, any other required information, for example, the start of pulse generation can be conveyed to the ALC 230.

If both parties have detected that only 3 wires are available for the interface, the interface wire that was previously applied for power/clock only is also used for communication. This might require that the electronics of the communication and power/clock module 217, 237 on one or both sides of the interface is reconfigured and/or expanded with (enabled) additional circuitry so that the clock can be extracted from the data stream on the ALC side again. For this, clock and data recovery (CDR) circuits known to the man skilled in the art of electronics can be applied. Thus in this 3-wire configuration, the first (available) wire is used for interface ground, the second for power/clock and communication and the last one for stimulation only.

If only two wires are left, one can resort to time-division multiplexing to transport both stimulation signals and the single power/clock/communication stream from IPG 210 to ALC 230. When the ALC cable monitor/checker 233 detects that a stimulation pulse has ended, the ALC ICPSM 231 is reprogrammed to connect the same line to the communication and power/clock module 237 of the ALC 230 and back again to the ALC CPSM 236 when a next stimulation pulse is due to be delivered. Thus the ALC communication and power/clock electronics 237 is reconfigured once more so that it can handle an interrupted power/clock/communication stream and also the IPG communication and power/clock circuit 217 is appropriately reconfigured and controlled by the IPG interface controller 212. A man skilled in electronics can find various solutions in literature to achieve this.

Finally, if only a single interface wire remains, one could use the conductive body as ground for both ALC 230 and IPG 210 if both the (conductive) IPG 210 and ALC 230 casings are in galvanic contact with the body. The body can be viewed as a fifth wire in the outlined example and the ALC rectifier 234a can be extended with another set of rectifier diodes connected to the ALC 230 casing to implement this. Time division multiplexing can be applied on the last remaining interface wire on both IPG 210 and ALC 230 side in the same way as for the 2-wire interface configuration.

AC Interface Signals and DC Blocking Capacitors

FIG. 11 shows ALC electronics coupled to the interface cable via a set of (external) DC blocking capacitors 330a except for the (dedicated) interface ground wire 221. A similar architecture can be used on the IPG side, including a direct connection between IPG ground and the IPG enclosure. Shown in FIG. 12 are the ALC enclosure 330', ALC electronics 330, a supply finder 335, an ALC ground module 339, and an AC power start-up module 334, the interface cross-point switch matrix 331 and an additional cross point switch matrix 338 with switches 338a. Not all ALC electronics is shown.

In neurostimulators and other implants, series capacitors are often used to block DC currents through terminals that are either directly (e.g. intended function) or indirectly (e.g. due to risk of potential hardware failure or leaking connectors) exposed to body tissue. An example of the use of DC blocking capacitors 330a on the ALC side is shown in FIG. 11, where only the modules relevant for this discussion are depicted. The shown DC blocking capacitors 330a can be (external) discrete components or they can be (part of) an integrated passive device or chip. DC blocking capacitors can be applied in a similar way on the IPG side of the interface.

FIG. 12 shows the modified power start-up module 334 of the ALC electronics 330 of FIG. 11 with a multi-phase half-wave rectifier 334a that is capacitively coupled to the interface cable 220 and permanently to the ALC enclosure 330' via connection point 330c and to ALC ground 330a. Furthermore, there is a voltage conversion (boosting) means in the form of a substrate charge pump part 334b which uses a charge pump 334g to bias the substrate; it receives power from the ALC power supply 334c.

The use of DC blocking capacitors 330a implies that the ALC electronics, including the power-start-up module 334, needs to be able to cope with AC interface signals. An AC variant of the ALC power start-up module is shown in FIG. 12. The multi-phase rectifier has been replaced by a multi-phase half-wave rectifier 334a with, at least in this example, three independent inputs where each input is capacitively coupled to a wire of the interface cable 220 as is shown in both FIG. 11 and FIG. 12. The common ground of the half-wave rectifier 334a is directly and permanently connected to the ALC enclosure 330' via connection point 330c and to ALC ground 330a.

The (dedicated) ground interface wire 221 is directly (no series DC blocking capacitors) connected to the IPG ground module. An AC voltage is put on the next available interface wire by the IPG interface start-up module to start the restoration of power to the ALC. This AC voltage is rectified by the half-wave rectifier 334a of the ALC power start-up module 334 and serves as a temporary power supply to the ALC. Next, as before, the supply finder, now capacitively coupled and therefore slightly modified, detects which line is used to supply AC power to the ALC, while a ground detector (not shown), for example, as part of the ALC cable monitor/checker or separately via a ground finder module, verifies if the (dedicated) interface ground wire 221 is indeed connected to IPG ground.

If it is confirmed that the (dedicated) interface ground wire 221 is connected to IPG ground, it is connected to the ALC ground module 339 by closing the cross-point switch 338a between the interface ground wire 221 and the ALC ground module 339 in cross point switch matrix 338 as depicted in FIG. 11. This action short-circuits the parallel ground return path via the body. If it turns out that the (dedicated) ALC ground interface wire 221 is not connected to IPG ground, for example, because the ground wire is broken (open-circuited), the body is (continued to be) used as ground return.

Next, as before, the identified interface supply wire is connected to the communication and power/clock module of the ALC and on command of the ALC interface controller, internally with the power/clock submodule to restore (permanent) power to the ALC. The communication and power/clock module is capacitively connected to the interface cable 220, and therefore, some hardware modifications might be needed. Those and other modifications of the ALC electronics due to the AC instead of DC coupling of the interface cable are known to a person skilled in the art of electronics.

Finally, the multi-phase half-wave rectifier 334a with rectifier diodes 334e, 334f is effectively decoupled from the interface cable 220 by shorting its inputs to ALC ground 330a via the NMOST short-circuit switches 330h that are under control of the ALC interface controller via a switch driver 334d as shown in FIG. 10. The grounded series capacitors 330b to the multi-phase rectifier 334a are the only loading of the interface cable that remains of the ALC power start-up module after activation of the NMOST switches 334h. The interface (re)configuration process can subsequently proceed along the same lines as already described for a DC coupled interface cable.

If desired, the ALC (interface) electronics can be modified depending on the application environment and design requirements:

1. One could replace the cross-point switch 338a between the (dedicated) ground interface wire 221 and the ALC ground module 339 with a hard wired connection. This short-circuits the ground return path via the body, and therefore, (almost) no body current flows as long as the (dedicated) ground wire 221 is still intact. One could also opt to remove the body return option from the design completely.
2. If a grounded ALC enclosure 330' is not wanted in normal operation, a circuit breaker can be inserted between the multi-phase half-wave rectifier 334a and the ALC ground and supply lines 330a, 330b in a way similar to the solutions shown in FIG. 8a and FIG. 8b.
3. If the (dedicated) ground interface wire 221 cannot be used, for example, because it is broken, and one does not want to use the body or cannot use the body as permanent ground return path, the interface can still be restored if not only the (dedicated) ground wire but also the other interface cable wires are coupled to the ALC ground module 339 via cross-point switches as highlighted by the dashed switches 338a in FIG. 11, because with those cross-point switches present, another cable wire can be selected as interface ground wire. The same strategy can be implemented on the IPG side of the interface so that a direct (no series DC blocking capacitors) ground connection between IPG 210 and ALC 230 can be restored and the body return path does not have to be used permanently.

Note that if a shielded cable is used between IPG 210 and ALC 230 that this shield can also be used and seen as just another cable interface wire, and therefore, can be treated in the same way as the other, actual, interface cable wires 221, 222, 223, 224.

Handling of Cable Interface Fault Conditions

The basic interface fault conditions are interface wires that are open-circuited, short-circuited, softly connected or a combination of these conditions:

1. Before the power restoration process starts, short circuits on the IPG side 210 of the interface cable 220 can easily be detected, for example by the IPG cable monitor/checker 213, in a way that does not trigger the ALC power start-up module 334. The IPG ICPSM 211 can be programmed in a way that the shorted interface wires are effectively treated and seen as a single wire. Shorts on the ALC side 230 can be detected by the ALC cable monitor/checker 233 during the power restoration and/or interface (re)configuration process.
2. In a similar fashion, soft connections i.e. low-ohmic connections between interface wires can be detected, including leakage paths to the body. The affected interface wires can be shorted together and, for example, be used as the interface ground wire. Another option is to leave those wires floating that are in direct contact with the body.
3. Interface wires that are broken (open-circuited) can most easily be detected when no acknowledgements are received on a line in time. For example, if the IPG 210 puts a voltage on a line to signal to the ALC 230 that the line is available for the interface and the IPG 210 does not receive a load modulation acknowledgement from the ALC 230 in time, it concludes that the line is broken. This same conclusion is reached on the ALC side 230 because no voltage is detected on the broken line. Another example is that the IPG 210 detects that the interface does not start-up despite the fact that a supply voltage is provided. Another available wire can be taken to start-up the interface and to detect which wire is defect.
4. Two interface wires that are detected to be shorted on one side of the interface do not have to be on the other side of the interface because a wire can both contain an open and a short. As a result, a wire can be shorted to another on one side and left floating on the other side of the interface.

Simple handshaking and easy measurements are sufficient to detect cable defects, while the availability of an ICPSM on both sides of the interface adds a lot of flexibility in the way those cable defects can be taken care of.

Thus it becomes clear from this embodiment that one can make a pre-agreement on how to distribute the needed and/or desired interface functions across an interface cable 220 if both parties know how many and which wires are available for the interface and which function is put on which wire where one can pre-agree to use an increasing interface wire number for the assignment of interface functions. It might require a reconfiguration of the interface electronics for each of the potentially appearing interface configurations (in our example, the 4/all-wire, 3-wire, 2-wire, 1-wire interface configurations were treated i.e. all possibilities) and above all, the proper use of the flexibility offered by the ICPSM matrices 211, 231 on both sides of the interface.

The invention claimed is:

1. A medical system comprising:
   a first module comprising a first distributing device;
   a second module comprising a second distributing device, wherein the second distributing device is connected to a lead comprising a plurality of electrodes;
   a first interface controller within the first module and configured to control the first distributing device;
   a second interface controller within the second module and configured to control the second distributing device; and
   two or more lines electrically connecting the first distributing device of the first module with the second distributing device of the second module, wherein the two or more lines are configured such that each line of the two or more lines is at least one of associated with at least one specific functionality or configured to connect at least one first connection point of a set of first connection points of the first module with at least one second connection point of a set of second connection points of the second module, wherein:
   the first distributing device and the second distributing device are configured to at least one of:
   (A) group at least two lines of the two or more lines to at least one of: the at least one specific functionality, or between at least one first connection point of the set of first connection points of the first module and at least one second connection point of the set of second connection points of the second module, or
   (B) change at least one line of the two or more lines from a first functionality of the at least one specific functionality to a second functionality of the at least one specific functionality.

2. The medical system of claim 1, wherein at least one of the first interface controller or the second interface controller are configured to detect that one line of the two or more lines is unusable for its purpose and, responsive to the detection, control the first distributing device and the second distributing device to at least one of group or change the at least one specific functionality of the one line unusable for its purpose onto one or more other lines of the two or more lines.

3. The medical system of claim 1, wherein at least one line of the two or more lines comprise at least one of a pulse generator line being connectable to a pulse generator output, a data input line, an output line, a power line, a clock line, or a connection line for ground.

4. The medical system of claim 1, wherein at least one line of the two or more lines is a connection line for ground, and wherein the first distributing device and the second distributing device are configured to replace the connection line for ground with at least one conductive part configured to contact tissue of a patient and in conductive contact with at least a portion of the medical system.

5. The medical system of claim 1, wherein the first distributing device and the second distributing device each comprise at least one cross-point switch matrix, and wherein the medical system further comprises at least one cable monitor that is configured to monitor a usability of the two or more lines for at least one of a resistance of the two or more lines or one or more short-circuits between different lines of the two or more lines.

6. The medical system of claim 1, further comprising at least one of a first memory or a second memory configured to store a mapping between a number of useable lines and a configuration of the first distributing device and the second distributing device, and wherein the first interface controller and the second interface controller are configured to control the respective first distributing device and the second distributing device based on the configuration information stored in at least one of the first memory or the second memory.

7. The medical system of claim 1, wherein:
   the first interface controller is at least one of connected with an interface start-up unit that is connected with the first distributing device and that is configured to provide one of a DC or an AC supply voltage to at least one line of the two or more lines, or connected with a ground unit that is connected with the first distributing device and that is configured to provide ground to at least one line of the two or more lines, and
   the second interface controller is at least one of connected with a power start-up unit that is connected to the second distributing device and that is configured to extract at least one of a supply voltage or a ground from the two or more lines, or connected with at least one of a supply/ground finder unit or a supply finder unit that is connected to the second distributing device.

8. The medical system of claim 7, wherein the interface start-up unit, the power start-up unit, and the supply/ground finder unit are each configured to be active only during a reconfiguration period during which at least one of the first distributing device or the second distributing device reconfigures the two or more lines.

9. The medical system of claim 1, wherein:
   the medical system comprises a deep brain stimulation system,
   the first module comprises an implantable pulse generator,
   the second module comprises an active lead can of the deep brain stimulation system, the active lead can coupled to the lead comprising the plurality of electrodes,
   the first distributing device is located in a first housing of the first module, and
   the second distributing device is located in a second housing of the second module.

10. The medical system of claim 1, wherein the medical system is configured to at least one of provide neural recording or deep brain stimulation.

11. A method for communicating a plurality of signals over a plurality of lines electrically connecting a first distributing device of a first module of a medical system to a second distributing device of a second module of the medical system, the method comprising:
    measuring at least one of one or more resistances between different lines of the plurality of lines or one or more resistances along one or more lines of the plurality of lines;
    determining which lines of the plurality of lines are usable based on the measuring; and
    configuring the first distributing device and the second distributing device such that the plurality of signals is transferred over those lines of the plurality of lines that have been determined to be useable, the first distributing device and the second distributing device being configured to at least one of:
    (A) group some lines to at least one of the at least one specific functionality or between at least one first connection point of a first set of connection points of the first module and at least one second connection point of a second set of connection points of the second module, or (B) change at least one line of the plurality of lines from a first functionality of the at least one specific functionality to a second functionality of the at least one specific functionality.

12. The method of claim 11, wherein:
the plurality of lines connect an implantable pulse generator of the first module to an active lead can of the second module, and
the first module comprises the first distributing device and the second module comprises the second distributing device.

13. The method of claim 11, further comprising detecting which of the lines of the plurality of lines are configured to supply power and ground.

14. The method of claim 11, further comprising performing time-division multiplexing to transport two or more signals of the plurality of signals over a single line of the plurality of lines.

15. The medical system of claim 1, further comprising a switch matrix configured to connect one or more electrodes of the plurality of electrodes of the lead to the second distributing device, the switch matrix being distinct from the first distributing device and the second distributing device.

16. A medical system comprising:
a first module;
a second module, wherein the second module is connected to a lead comprising a plurality of electrodes;
a first interface controller within the first module and configured to control the first distributing device;
a second interface controller within the second module and configured to control the second distributing device;
two or more lines electrically connecting the first module with the second module, wherein the two or more lines are configured such that each line of the two or more lines is at least one of associated with at least one specific functionality or configured to connect at least one first connection point of a set of first connection points of the first module with at least one second connection point of a set of second connection points of the second module;
first means for at least one of:
 (A) grouping at least two lines of the two or more lines to at least one of the at least one specific functionality or between at least one first connection point of the set of first connection points of the first module and at least one second connection point of the set of second connection points of the second module, the first means for grouping or redistributing located within the first module, or
 (B) changing at least one line of the two or more lines from a first functionality of the at least one specific functionality to a second functionality of the at least one specific functionality, and;
second means for at least one of:
 (A) grouping at least two lines of the two or more lines to at least one of the at least one specific functionality or between at least one second connection point of the set of second connection points of the second module and at least one first connection point of the set of first connection points of the first module, the second means for grouping or redistributing located within the second module, or
 (B) changing at least one line of the two or more lines from the first functionality of the at least one specific functionality to the second functionality of the at least one specific functionality.

17. The medical system of claim 16, further comprising:
means for detecting that one line of the two or more lines is unusable for its purpose; and
means for, responsive to the detection, controlling the first and second means for at least one of grouping some of the lines or changing the at least one specific functionality of the one line unusable for its purpose onto one or more other lines of the two or more lines.

18. The medical system of claim 16,
further comprising means for housing the two or more lines and connecting the first means for grouping or changing to the second means for grouping or changing.

* * * * *